United States Patent [19]
Byrne et al.

[11] Patent Number: 5,305,761
[45] Date of Patent: Apr. 26, 1994

[54] AMBULATORY MONITOR

[75] Inventors: Shaun C. Byrne; Simon J. Large; Richard J. Riggs; Peter J. Narramore, all of Oxon, Great Britain

[73] Assignee: Oxford Medical Limited, Osney Mead, United Kingdom

[21] Appl. No.: 699,212

[22] Filed: May 13, 1991

[30] Foreign Application Priority Data

May 14, 1990 [GB] United Kingdom ............... 9010774

[51] Int. Cl.$^5$ ............................................. A61N 1/08
[52] U.S. Cl. .............................. 128/697; 364/413.06
[58] Field of Search .......................... 128/697, 701; 364/413.06

[56] References Cited

U.S. PATENT DOCUMENTS

| | | | |
|---|---|---|---|
| 4,248,244 | 2/1981 | Charnitski et al. | 128/706 |
| 4,291,703 | 9/1981 | Kelen | 128/711 |
| 4,532,934 | 8/1985 | Kelen | 128/697 |
| 4,838,278 | 6/1989 | Wang et al. | 128/697 |
| 4,905,706 | 3/1990 | Duff et al. | 128/701 |

FOREIGN PATENT DOCUMENTS

| | | |
|---|---|---|
| 0280530 | 8/1988 | European Pat. Off. . |
| 2757983 | 6/1991 | Fed. Rep. of Germany . |

OTHER PUBLICATIONS

R. E. Bonner, "Portable EGC Event Detector", *IBM Technical Disclosure Bulletin*, 25 (No. 7A), 3412-3413 (Dec. 1982).

S. K. Doran, "Method of Detecting Pacemaker Spikes In An Electrocardiograph Signal And Uniquely Encoding Them On An Ambulatory Recorder", *IBM Technical Disclosure Bulletin*, 26 (No. 11), 6013-6015 (Apr. 1984).

Primary Examiner—William E. Kamm
Assistant Examiner—Scott M. Getzow
Attorney, Agent, or Firm—Hoffmann & Baron

[57] ABSTRACT

An ambulatory monitor for monitoring the action of a pacemaker and the cardiac response of a patient fitted with a pacemaker. The monitor comprises a detection electrode coupled in use to the patient for detecting pacemaker pulses and cardiac responses; an analyser connected to the detection electrode for a) analysing the relationship between the detected pacemaker impulses and cardiac responses, b) analysing the shape and timing of the cardiac responses, and c) generating corresponding data signals; and a recorder for recording the data signals.

13 Claims, 1 Drawing Sheet ically, ECG signals have been monitored by using apparatus positioned beside a bed on which the patient lies. One problem which arises is where the patient has a pacemaker since conventional ECG monitors can respond to normal pacemaker beats by sounding an alarm. One method for overcoming this problem is described in EP-A-0280530. The technique described is satisfactory for the purposes of a stationary monitor but is not readily adaptable to ambulatory monitors.

AMBULATORY MONITOR

FIELD OF THE INVENTION

The invention relates to an ambulatory monitor.

DESCRIPTION OF THE PRIOR ART

The invention is particularly concerned with apparatus for monitoring cardiac responses in the form of ECG signals. Histor Ambulatory monitors have been developed over a number of years to monitor in particular the cardiac response of a patient to whom the monitor is mounted. Historically, such monitors have incorporated a magnetic tape or the like which is coupled via a detector to electrodes mounted in use to the patient. Heart beats are detected by the electrodes with corresponding signals being fed to and recorded on the magnetic tape to generate a conventional electro-cardiograph (ECG). Once the tape is full it is removed from the monitor and positioned in an analyser through which it is then run, often at relatively high speed, so that the ECG can be read off the tape and then analysed to detect for example, anomalous heart beats.

In a more recent development, the present applicants have devised an ambulatory ECG monitor in which instead of simply recording the ECG signal itself, the incoming signal is analysed by an analyser provided in the ambulatory monitor. The analyser classifies each beat and allocates to it a template number which most closely represents the shape of the beat. Data is then laid down on a data track of the magnetic tape which defines the time, type and shape of the beat concerned. At the same time the original ECG signals are recorded on separate tracks. The advantage of this is that most of the analysis is carried out in real time with the result that when the tape is removed from the monitor the data track can very quickly be utilized to generate data which can be displayed for analysis by a doctor for the purposes of diagnosis. The advantage of this real time analysis can be seen from the fact that a tape recording 24 hours of an ECG only would take about 20 minutes to analyse whereas if the analysis is performed in real time then the final summary can be obtained in a few minutes.

Many patients whose ECG is monitored are fitted with pacemaker devices. These devices generate impulses to cause the heart to beat and it is important to be able to monitor not only the heart beats themselves (as in conventional ECG analysis) but also the relationship between pacemaker spikes and the heart beats. Thus, certain types of abnormality can occur where for example a pacemaker impulse or spike occurs too long after a heart beat or where a heart beat is slow to follow a pacemaker spike. Ambulatory systems to enable both pacemaker spikes and heart beats to be monitored are described in US-A-4291703 and US-A-4532934. One of the problems with monitoring pacemaker spikes is that these cannot easily be laid down on tape in the same manner as a conventional ECG. The two patents mentioned, which both relate to the so-called "retrospective" systems convert the pacemaker spike into a distinctive synthesized signal which can be recorded on tape. This synthesized or "stretched" signal is recorded on one channel while the ECG signals themselves are recorded on another channel. After use, the tape is down loaded and mounted into an analysing device which then carries out a retrospective analysis of the ECG waveform but relates this to the pacemaker spikes recorded on the other channel. This device suffers from the same problems as other retrospective analysers namely the time taken to analyse the resultant tape but additionally has the problems of needing equipment to generate the stretched or synthesized spike signals and needing equipment to detect the synthesized signals.

SUMMARY OF THE INVENTION

In accordance with the present invention, an ambulatory monitor for monitoring the action of a pacemaker and the cardiac response of a patient fitted with the pacemaker comprises detection means coupled in use to the patient for detecting pacemaker pulses and cardiac responses; an analyser connected to the detection means for a) analysing the relationship between the detected pacemaker impulses and cardiac responses, b) analysing the shape and timing of the cardiac responses, and c) generating corresponding data signals; and recording means for recording the data signals.

We have devised a new ambulatory monitor which is capable of monitoring the action of a pacemaker and the cardiac response but which additionally performs a real time analysis by virtue of the presence of the analyser within the ambulatory monitor itself.

In the basic application, each pulse, whether it be a pacemaker impulse or heart beat, and the data signals are recorded. The data signals typically define the time of occurrence of the impulse, the type of impulse (pacemaker or cardiac) and the shape of the impulse or response. In some cases the analyser can also determine the relationship between the detected pacemaker impulses and cardiac responses. This data defining impulse and response types can then simply be down loaded and displayed. A complication which can arise in some circumstances is that it may not be possible to record all the data. For example, in a typical application, it may only be possible to store data signals defining impulses or responses up to a sustained rate of 200 per minute. Since it is essential to store information relating to the cardiac responses, the analyser may be adapted to generate a composite data signal in the case where a pacemaker impulse and a cardiac response are normally separated. Thus, where there are no abnormal conditions, a single data signal is generated which defines, for example, the time of occurrence and type of heart beat using a special value which indicates that the heart beat was within a preset normal time range of the preceding pacemaker spike. Of course, there are several different ways in which this composite signal could be generated based either on the time of occurrence of the heart beat or pacemaker spike.

Preferably, the recording means also records the cardiac responses. This conventional recording of the ECG is helpful in case the doctor wishes to look at the raw ECG for any reason.

Typically, the recording means comprises first and second recorders, the first recorder comprising for example a magnetic tape recorder for recording the data signals and, where appropriate, the ECG, and the second recorder comprising one or more counters for counting respective abnormal conditions. Other forms of recording means, particularly solid state recorders and digital audiotape, could also be used.

The data signals may have various forms but a typical data signal may comprise three portions, one of which defines the time of occurrence of the impulse or response, the second of which defines the type of beat (i.e. pacemaker impulse or cardiac response) and the third portion defining a template defining the shape of the beat concerned.

BRIEF DESCRIPTION OF THE DRAWINGS

An example of an ambulatory monitor according to the invention will now be described with reference to the accompanying drawings, in which.

DETAILED DESCRIPTION OF THE EMBODIMENT

Figure 1:
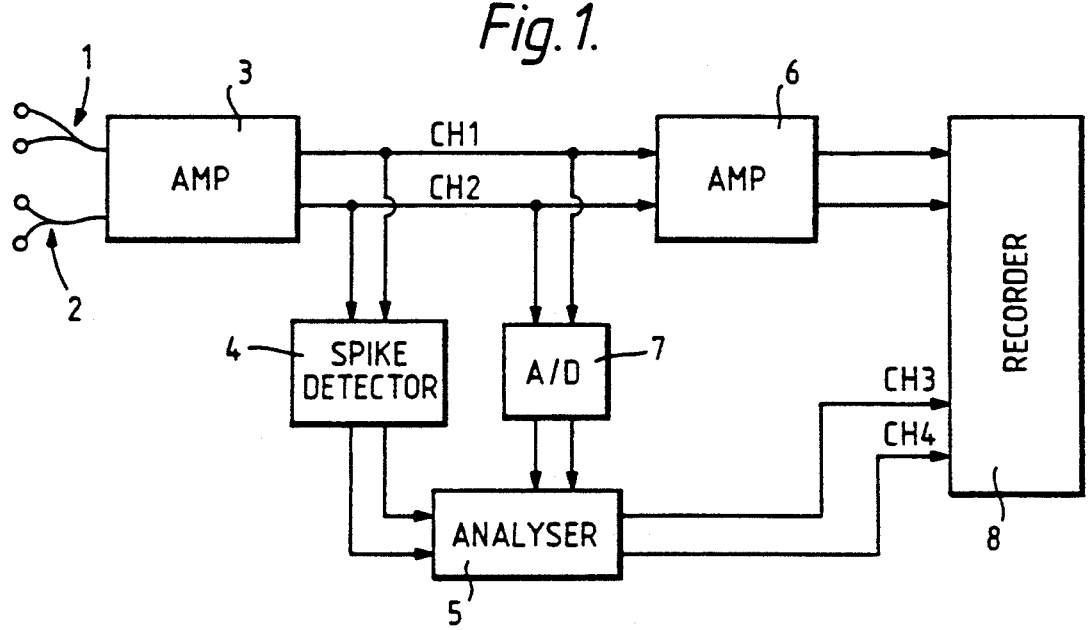
FIG. 1 is a block diagram of the apparatus.

The monitor shown in FIG. 1 comprises a housing (not shown) of a conventional type which can be strapped to a patient and to which are connected two pairs of differential electrodes 1, 2. The electrodes pass electrical signals corresponding to pacemaker impulses and cardiac responses to a first stage amplifier 3 mounted in the housing, the amplified signal being fed to a spike detector 4. The spike detector 4 detects the arrival of an electrical impulse representing a pacemaker spike and on detecting such a spike generates a digital timing signal which is fed to an analyser 5 constituted by a suitably programmed microprocessor. The amplified signals are also fed to a second stage amplifier 6 and are applied to an A/D convertor 7 which is coupled to the analyser 5. The outputs from the amplifiers 6 which will consist of analog signals are fed to a recorder which could be a solid state device but in this example is a conventional audio magnetic tape recorder 8 for recordal in two channels (channels 1 and 2) of an audio tape. Since the frequencies involved in the pacemaker spikes are too high for the purposes of reliable recording on tape, the signals will include little record of the spikes.

The analyser 5 generates data signals which are fed to channels (CH3, CH4) of the tape recorder 8 for recordal on respective tracks of the tape. Channel CH3 records data defining the shape and time of occurrence of pacemaker spikes and heart beats as will be described below while the channel CH4 records a time marker at regular intervals as well as "patient events" which are advised to the analyser by the patient himself.

Figure 2:
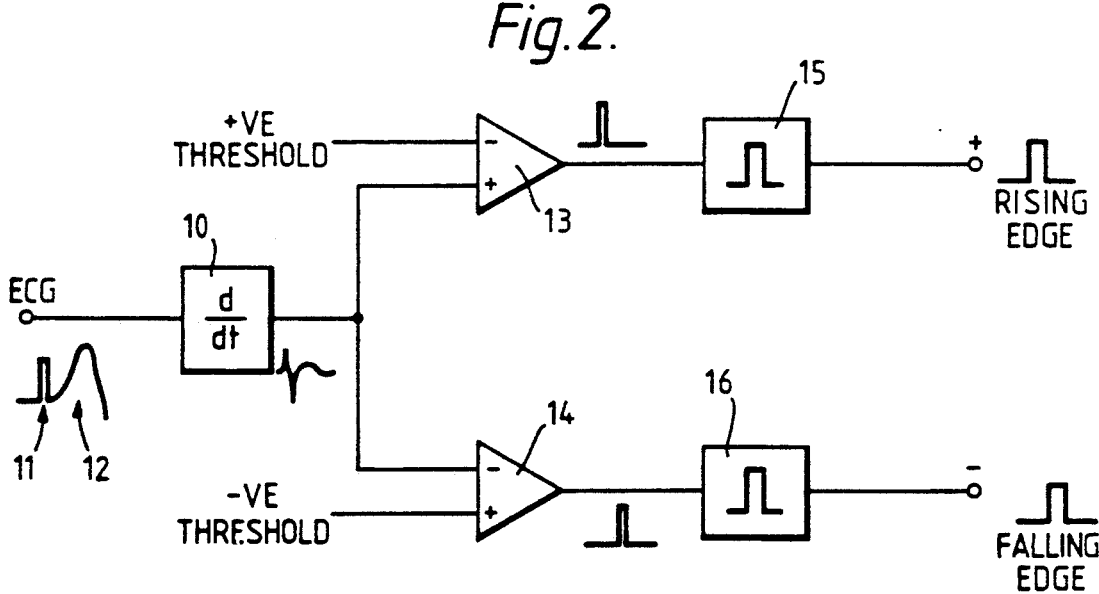
FIG. 2 is a block diagram of the spike detector of FIG. 1.

The spike detector 4 is shown in more detail in FIG. 2. The detector comprises a differentiator 10 to which the ECG signal is fed. As can be seen in FIG. 2, the ECG signal comprises fast rising and falling edges 11 corresponding to a pacemaker spike and another signal 12 corresponding to the cardiac response. The fast rising and falling edges of a pacemaker spike 11 will produce a much larger differentiated signal than the underlying ECG signal 12 which changes relatively slowly.

The differentiated signal from the differentiator 10 is fed to a pair of comparators 13, 14 which generate an output only when the differentiated signal exceeds the respective comparator threshold. The comparator 13 has a positive threshold for detecting the rising edge of the spike, and the comparator 14 has a negative threshold for detecting the falling edge. Each comparator output is passed to respective pulse generator 15, 16 so that a single pulse is generated when the threshold is exceeded. The pulses from the rising and falling edge detectors are then passed to the analyser 5.

Various different types of analysis may be performed by the analyser 5. A typical set of analyses will be described below in connection with FIG. 3.

Figure 3:
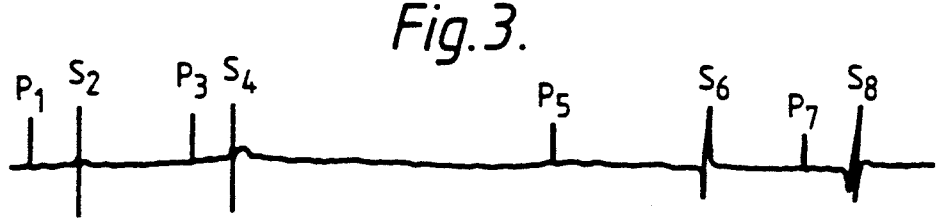
FIG. 3 illustrates an example of a sequence of pacemaker impulses and cardiac responses.

FIG. 3 illustrates a succession of pacemaker impulses and cardiac responses with pacemaker impulses being labelled P and heart beats being labelled S. In this case, all the heart beats are supraventricular, that is the heart beats are acceptable in themselves but the analyser could also detect so-called ventricular beats which are anomalous.

The time intervals between P1, S2, P3 S4, P7 S8 are short, as they should be, the pacemaker spike resulting in a heartbeat within a normal time interval.

The P5 S6 combination demonstrates two types of malfunction. Firstly, P5 follows a long way after S4. Pacemakers are supposed to prevent pauses in the heart rhythm, and this is known as "Delayed Output". Secondly, the beat S6 was slow to follow the preceding spike.

The analyser 5 receives from the spike detector 4 signals which indicate timing of pacemaker pulses and receives from the A/D converter 7 digital versions of the cardiac responses. The analyser can therefore monitor the type of cardiac response and its timing relationship with the pacemaker impulses and determine firstly any abnormal conditions such as those mentioned above, and secondly generate data signals defining the form of each impulse or response.

The data track (CH3) records data signals of the form:

T1/P/TEM60, T2/S/TEM4, T3/P/TEM etc.

Each signal has three components. The first, eg T1, indicates the time of occurrence of the impulse or response relative to a preceding time marker on channel CH4, the second eg P, indicates the type of impulse or response; and the third, eg TEM60, is a template number defining the shape of the impulse or response. In the case of the first signal relating to impulse P1, the template number 60 is chosen since this falls outside the range of numbers allocated to normal beat shapes.

As has been mentioned above, particularly in the case of recording on a magnetic tape, there is a maximum to the number of data signals which can be recorded in a given time interval. In conventional ECG recorders the maximum containable heart rate is a sustained rate of about 200 beats per minute. Since the pacemaker spikes are encoded as beats that limitation effectively drops to about 100. To deal with this, a special template value, eg TEM28, can be set which is recorded in association with a data signal defining a heart beat, that indicates that the heart beat occurred within a normal, preset time range from the preceding pacing spike. Thus, an example of a data signal of this type would be:

T2/S/TEM28 which means at T2 there was a supraventricular beat preceded by a pacing spike within a preset normal time range.

Once the magnetic tape is full it is removed from the tape recorder 8 and inserted into a reading device of conventional form which can simply read the data on the data track and display it for analysis.

In one example, the analyser 5 operates as follows. The ECG is analysed in two phases. The first is to detect the presence of a beat using slope crossing and noise rejection criteria on both channels of ECG. Basic principles of this technique are described in the paper "A Single Scan Algorithm for QRS-Detection and Feature Extraction", W.A.H.Engelse and C.Zeelenberg, Computers in Cardiology, 1979. The second phase is to compare the most recently detected beat with templates formed from previously detected beats, using a correlation method. If the beat correlates well with an existing template, it is classified with that template number and if the EC signal is clean, the beat shape is averaged into the template shape. If it does not correlate well with any of the existing templates and the signal is clean, a new template is formed from that beat. If the beat does not correlate well with any template, but the signal is too noisy to form a new template with, then the beat is classified with the template it fits best, but it is marked as being a poor match. When the tape is replayed later, the replay analyser may be able to recorrelate the poorly matched beats with the full set of templates from the entire recording to try to find a better match.

The pulses from the spike detector are also analysed. Since a pacemaker spike normally consists of a short pulse, typically less than 2 msec, the analyser can improve the noise rejection by allowing only pairs of rising and falling edge pulses separated by less than 2 msec to qualify as pacemaker spikes. However, some pacemakers generate spikes which have a less pronounced falling edge which can fail to meet the normal threshold setting. For this reason, a high sensitivity mode can be programmed in the analyser whereby either a single edge or a pair of edges will qualify.

If a spike is detected a short time before a beat is detected, the beat is assumed to be paced. If two spikes occur close together and before the beat, the beat is assumed to be dual-paced, ie. both chambers are paced by a dual chamber pacemaker. Each beat is thus given a pacing classification of unpaced, single-paced or dual-paced. Each beat detected will be correlated only with templates containing other beats of the same pacing classification. By this means, if the heart rate is too high to permit both the beats and the spikes to be recorded and the spikes are omitted, paced beats can still be identified as such from their template number.

We claim:

1. An ambulatory monitor for monitoring the action of a pacemaker and cardiac response of a patient fitted with a pacemaker, the monitor comprising:
    a pair of electrodes for coupling to a patient to monitor pacemaker pulses and analog ECG signals, said analog ECG signals being amplified for recording;
    a spike detector for detecting said pacemaker pulses from said electrodes, said spike detector having means for generating a first signal indicating the occurrence of said pacemaker pulses;
    an A/D converter for detecting said amplified analog ECG signals from said electrodes, said A/D converter generating a second signal, said second signal is a digital version of said analog ECG signal indicating the occurrence of said amplified analog ECG signal;
    an analyzer connected to said spike detector and said A/D converter, said analyzer comprising:
    a) means for determining a time of occurrence of said pacemaker pulses from said first signal, and means for determining a time of occurrence of said ECG signal from said second signal;
    b) means for determining in real time, a timing relationship between said first and second signals;
    c) means for analyzing in real time, the timing relationship and a shape of said second signal; and
    d) means for generating in real time, composite data signals defining:
        a time of occurrence of each of said first and second signals;
        a first and a second indication identifying said first signal as said pacemaker pulse and said second signal as said ECG signal; and
        a third indication denoting the shape of said first and second signals; and
    recording means for recording said composite data signals on a first channel of said recording means.

2. A monitor according to claim 1, wherein said analyzer further comprises:
    means for generating in real time, a further indication denoting a second signal occurring within a normal, preset time range from a corresponding first signal and means for combining said further indication with said composite data signals for recording on said first channel of said recording means, in real time.

3. A monitor according to claim 1, wherein the recording means record said analog ECG signals on a second channel at the same time as the composite data signals are recorded on said first channel.

4. A monitor according to claim 3, wherein said analyzer further comprises:
    means for generating in real time, while said analog ECG signal is recorded, a fourth indication denoting the timing relationship between said first and second signals and means for combining said fourth indication with said composite data signals for recording on said first channel of said recording means, in real time, while said analog ECG signal is recorded on said second channel of said recording means.

5. A monitor according to claim 3, wherein said analyzer further includes:
    means for generating a time marker signal at regular intervals, said time marker signal being recorded on a third channel of said recording means, in real time, while said analog ECG signal is recorded on said second channel of said recording means.

6. A monitor according to claim 5, further comprising means for recording patient events, said patient events being input into said analyzer by said patient and recorded with said time marker on said third channel of said recording means.

7. A monitor according to claim 1, wherein said recording means is an audio tape recorder.

8. A method for monitoring the action of a pacemaker and cardiac response of a patient fitted with a pacemaker using an ambulatory monitor, the method comprising:
    attaching a pair of electrodes for coupling to a patient to monitor pacemaker pulses and analog ECG signals;

amplifying said analog ECG signals and said pacemaker pulses;

detecting said amplified pacemaker pulses using a spike detector;

generating a first signal from the spike detector for indicating the occurrence of said pacemaker impulses;

detecting said analog ECG signals by means of an A/D converter, said A/D converter generated a second signal indicating the occurrence of said analog ECG signal, said second signal is a digital version of said analog ECG signal;

processing said first and second signals by means of an analyzer, the processing steps comprising:
a) determining a time of occurrence of the pacemaker pulse from said first signal and determining a time of occurrence of the ECG signal from said second signal;
b) determining in real time, a timing relationship between said first and second signals;
c) analyzing in real time, the timing relationship and a shape of said second signal; and
d) generating in real time, composite data signals defining:

a time of occurrence of each of said first and second signals;

a first and second indications identifying said first signal as said pacemaker pulse and said second signal as said ECG signal;

a third indication denoting the shape of said first and second signals; and recording said composite data signals on a first channel of a recording means, in real time.

9. A method according to claim 8, wherein said amplified analog ECG signals are recorded on a second channel of said recording means while said composite data signals are being recorded on said first channel.

10. A method according to claim 9, wherein said method further comprises the steps of:
generating in real time, while said analog ECG signal is recorded, a fourth indication denoting the timing relationship between said first and second signals, and
combining said fourth indication with said composite data signals for recording on said first channel of said recording means, in real time, while said analog ECG signal is recorded on said second channel of said recording means.

11. A method according to claim 9, wherein said method further comprises the steps of:
generating a time marker signal at regular intervals, and
recording said time marker signal on a third channel of said recording means, in real time, while said analog ECG signal is recorded on said second channel of said recording means.

12. A method according to claim 11, wherein said method further comprises the step:
recording patient events, said patient events being input into said analyzer by said patient and recorded with said time marker on said third channel of said recording means.

13. A method according to claim 8, wherein said method further comprises the steps of:
generating in real time, a further indication denoting a normally time separated first signal and corresponding second signal, and
combining said further indication with said composite data signals for recording on said first channel of said recording means, in real time.

* * * * *